US008923569B2

(12) United States Patent
Duarte

(10) Patent No.: US 8,923,569 B2
(45) Date of Patent: Dec. 30, 2014

(54) SYSTEM FOR DIAGNOSIS OF PLANT ANOMALIES

(75) Inventor: Ricardo Junqueira Franco Duarte, Sao Paulo (BR)

(73) Assignee: BASF SE, Ludwigshafen (DE)

( * ) Notice: Subject to any disclaimer, the term of this patent is extended or adjusted under 35 U.S.C. 154(b) by 198 days.

(21) Appl. No.: 13/382,692

(22) PCT Filed: Jul. 5, 2010

(86) PCT No.: PCT/EP2010/059590
§ 371 (c)(1),
(2), (4) Date: Jan. 6, 2012

(87) PCT Pub. No.: WO2011/003881
PCT Pub. Date: Jan. 13, 2011

(65) Prior Publication Data
US 2012/0114187 A1 May 10, 2012

(30) Foreign Application Priority Data
Jul. 8, 2009 (BR) .................................... 0905641

(51) Int. Cl.
*G06K 9/00* (2006.01)
*G06F 19/00* (2011.01)

(52) U.S. Cl.
CPC ........ *G06F 19/3406* (2013.01); *G06F 19/3443* (2013.01)
USPC ....................................................... 382/110

(58) Field of Classification Search
CPC .................. G05D 1/0276; G05D 2201/0201; G05D 1/0287; G05D 2201/0216; G05D 2201/0207; G06F 19/3443; G06F 19/3406
USPC ................................................. 382/100, 110
See application file for complete search history.

(56) References Cited

U.S. PATENT DOCUMENTS

| 5,841,883 A | 11/1998 | Kono et al. |
| 6,014,451 A * | 1/2000 | Berry et al. ................ 382/110 |

(Continued)

FOREIGN PATENT DOCUMENTS

| JP | 09-262027 | 10/1997 |
| JP | 2002-176855 | 6/2002 |

(Continued)

OTHER PUBLICATIONS

Xin et al., "Development of a Distance Diagnostic and Identification System for Plant, Insect, and Disease Problems", Applied Engineering in Agriculture, 2001, vol. 17, No. 4, pp. 561-565, Search Report.

(Continued)

*Primary Examiner* — Shefali Goradia
(74) *Attorney, Agent, or Firm* — Brinks Gilson & Lione

(57) ABSTRACT

The present invention refers to a system for the diagnosis of plant anomalies which comprises at least: an acquisition device (1) capable of capturing images in real time of at least one sample of a plant to be diagnosed; a storage unit (2) comprised by a database of digitalized images (7) of samples of plants affected by anomalies and also comprised by a database of technical information (8) related to said anomalies; a human interface device (3) capable of displaying digitalized images of the plant samples; a human control device (4) capable of allowing for an active interaction between a user and the human interface device; and a processing unit (5) operatively associated to the acquisition device (1), to the storage unit (2), to the human interface device (3) and to the human control device (4). This processing unit (5) is configured to run a dedicated computer program (6) capable of: displaying the image of the sample of the plant to be diagnosed and the digitalized image of the sample of the plant filed in the database of images (7) from the storage unit (2) simultaneously in the human interface device (3); automatically providing information of at least, one product and/or method suitable for treating the anomaly diagnosed by means of the human interface device (3); and allowing for the graphic manipulation of the plant images shown in the human interface device (3) by means of the human control device (4).

13 Claims, 9 Drawing Sheets

(56) References Cited

U.S. PATENT DOCUMENTS

| | | |
|---|---|---|
| 8,229,467 B2 * | 7/2012 | Root et al. ................. 455/456.2 |
| 2002/0021828 A1 | 2/2002 | Papier et al. |
| 2008/0157990 A1 | 7/2008 | Belzer et al. |

FOREIGN PATENT DOCUMENTS

| WO | WO 99/21118 | 4/1999 |
|---|---|---|
| WO | WO02/11035 | 2/2002 |

OTHER PUBLICATIONS

International Search Report, PCT/EP2010/059590, mailed Sep. 23, 2010.
International Preliminary Report on Patentability, PCT/EP2010/059590, issued Jan. 10, 2012.
Dell™ Inspiron™ 1420 Owner's Manual, Model PP26L, Jun. 2007.

* cited by examiner ically a mistaken diagnosis may
SYSTEM FOR DIAGNOSIS OF PLANT ANOMALIES This application is a National Stage application of International Application No. PCT/EP2010/059590 filed Jul. 5, 2010, the entire contents of which is hereby incorporated herein by reference. This application also claims priority under 35 U.S.C. §119 to BR Patent Application No. PI0905641-6, filed Jul. 8, 2009, the entire contents of which is hereby incorporated herein by reference.

The present invention relates to a system for the diagnosis of plant anomalies, characterized in that it comprises:

- at least an acquisition device (1) capable of capturing images in real time of at least one sample of a plant to be diagnosed;
- at least a storage unit (2) comprising a database of digitalized images (7) of samples of plants affected by anomalies and also comprising a database of technical information (8) related to said anomalies;
- at least one human interface device (3) capable of displaying digitalized images of the plant samples;
- at least one human control device (4) capable of allowing for an active interaction between a user and the human interface device (3); and
- at least one processing unit (5) operatively associated to the acquisition device (1), to the storage unit (2), to the human interface device (3) and to the human control device (4), the processing unit (5) being configured to run a dedicated computer program (6) capable of:
  - allowing the display of the image of the sample of the plant to be diagnosed and the digitalized image of the sample of the plant filed in the database of images from the storage unit (2) simultaneously in the human interface device (3);
  - automatically providing information on, at least, one product and/or method suitable for treating the anomaly diagnosed by means of the human interface device (3); and
  - allowing for the graphic manipulation of the plant images shown on the human interface device (3) by means of the human control device (4).

In addition, the present invention refers to the use of a system as defined above for identifying plant anomalies. A preferred embodiment of the invention refers to the use of a system as defined above wherein the plant anomalies to be identified are caused by bacteria, virus, fungi, nematodes or insects.

More particularly, the present invention refers to a system capable of allowing the diagnosis, assessment and control of plant diseases by providing technical information and manipulate images which allow for analyzing external manifestations of these anomalies by means of a graphic interface.

BACKGROUND OF THE INVENTION

Normally, plant anomalies are manifested by changes in their morphology, physiology or behavior, and they may have biotic origin when caused by viruses, fungi, bacteria, nematodes, phytoplasmas or viroids, and/or abotic origin when caused by lack of nutrients (ex: mineral shortage) or improper environmental conditions such as high temperatures, soil composition, excessive humidity and/or presence of pollutants.

Anomalies in plants may impair the quality and/or quantity of production in crops. Even currently, in spite of the advances in science and phytopathology, considerable losses happen in the fields, resulting in significant losses to farmers.

In view of that, the diagnosis of plant anomalies and the appropriate treatment thereof by means of control measures are necessary so that these losses may be minimized. In this sense, identifying the problem at a premature stage is very important in order to allow for controlling the anomaly in the beginning of its surge, before it spreads in large scale, avoiding major problems.

However, such diagnosis is a relatively complex issue to farmers, agronomists, scientists, researchers and scholars in general, because a highly specialized technical knowledge is necessary. As a result, many professionals from different fields such as entomologists, pathologists, geneticists, specialists in soil, herbicides, fruit growing, etc are needed to carry out a respective diagnosis. In addition, the variety and amount of known anomalies is very high, to such an extent that manual research in books, magazines and other literatures for consultation requires considerable time and dedication. It is important to highlight that a mistaken diagnosis may lead to actions of control unsuitable for the treatment of anomalies, resulting in additional losses.

In view of that, people have sought after solutions to facilitate the identification of these anomalies, mainly through the study and analysis of their physiological manifestations.

For instance, North-American patent U.S. Pat. No. 5,841,883 describes a device and method capable of providing a diagnosis of plant anomalies through an automated graphic comparison (by computer) between images of the plant to be diagnosed and images of plants affected by anomalies contained in a digital database. In practice, automated comparison is susceptible to mistakes, because the captured images of the plants to be diagnosed must be compatible with the specified conditions and standards of color, brightness, contrast, and be at a predetermined position and angle. Thus, one image that does not meet these conditions and standards may lead the device/method to a mistaken diagnosis, which may result in inadequate treatment and, consequently, major losses to plantations. Moreover, automation requires a high processing capacity, that is, it raises the costs necessary for the implementation of this device/method, making it impossible for small farmers to use it.

North-American patent application US 2002/0021828 describes a system implemented on a webpage (ex: Microsoft Internet Explorer or Mozilla Firefox) which allows for visually comparing pictures of a plant to be diagnosed with pictures of plants affected by anomalies stored in a database. Such pictures are arranged adjacent to one another ("side by side"). Thus, unlike the automated device/method disclosed by document U.S. Pat. No. 5,841,883, comparison must be made by users visually. However, this system does not allow for manipulating and editing images through resources such as enlargement, reduction, notes, cuts, highlight, enhancement, etc—which are sometimes necessary for a more accurate comparative outcome—therefore limiting its usability. In addition to that, the images used for comparison are of static nature, that is, they are pictures which, in many cases, have not been properly taken, preventing a more accurate analysis. In this approach, the document does not specify procedures for capturing the photographic images. In other words, the use of static images also limits the usability of this system.

North-American patent U.S. Pat. No. 6,014,451, corresponding to the Brazilian application PI 9813086-2, also discloses a system for the diagnosis of plant anomalies by visually comparing images of a plant to the diagnosed, captured in real time, with images of plants affected by anomalies stored in a database. This system is different from the ones previously mentioned once it is capable of providing dynamic images (video) in real time and also allowing them to be manipulated and edited. However, this system requires the use of a plurality of proprietary computer programs such as Labview Pro, Adobe Photoshop, Microsoft Access and Microsoft Word, which apart from requiring a high processing capacity of hardware, does not optimize the data flow among its parts, once there is no dedicated computer program to control the main functions of the system. Besides, the costs for purchasing these programs make the implementation of the system expensive. Additionally, the recommendations on treatment for the anomalies are not automatically made, requiring the presence of a specialist able of recommending to users a product/method for treatment through phone calls, e-mails or letters, impairing practicality in general. Furthermore, the system defined in the above identified document requires the installation of expensive and structured remote laboratories, containing microscopes, photographic cameras and equipment for the cultivation of microorganisms close to the plantation site. From the images obtained at these remote laboratories, a central laboratory with specialists analyzes the images/and or additional data collected in the remote laboratories and, from then on, by means of specialists, it diagnoses possible diseases.

As this document dates back to 1998, at that time there was no sufficient technological advancement, in such a way that assembling the central laboratory and a plurality of remote laboratories with all the involved equipment requires costs which are so high that their practical application is unfeasible.

Thus, none of the state of the art documents mentioned above discloses a system/device/method for the diagnosis of plants anomalies by comparing their images, which combines good accuracy of identification/treatment, easy operation and low cost with the use of a reduced amount and variety of equipment, and high performance.

OBJECT OF THE INVENTION

The object of the present invention is to provide a low-cost computerized system of simple operation, capable of allowing the diagnosis and treatment of plant anomalies by manipulating images and technical information arranged on a graphic interface, enabling the identification and analysis of physiological manifestations of such anomalies, in a quick and easy manner.

Another object of the present invention is also that such a system is to be capable of providing information and recommendations on products for the treatment and control of a certain anomaly, without the need of having the system's user to directly interact with a specialist. Yet another object of the present invention is to have all the major functionalities of such a system controlled by a dedicated computer program, in order to optimize the processing and flow of data, as well as exclude the need of purchasing proprietary programs from third parties, thus reducing even more the implementation costs.

SUMMARY OF THE INVENTION

The object of the present invention is achieved through the supply of a system for diagnosing plant anomalies which comprises at least: one acquisition device capable of capturing images in real time of at least one sample of a plant to be diagnosed; a storage unit comprising a database of digitalized images of samples of plants affected by anomalies and also comprising a database of technical information related to said anomalies; a human interface device capable of displaying the digitalized images of the plant samples; a human control device capable of allowing an active interaction between a user and the human interface device; and a processing unit operatively associated with the acquisition device, with the storage unit, with the human interface device and with the human control device.

This processing unit is configured to run a dedicated computer program capable of: displaying the image of the sample of the plant to be diagnosed and the digitalized image of the sample of the plant filed in the database of images from the storage unit simultaneously at the human interface device; automatically providing information on, at least, one product and/or method suitable for treating the anomaly diagnosed by means of the human interface device; and allowing for the graphic manipulation of the plant images shown in the human interface device by means of the human control device.

BRIEF DESCRIPTION OF THE DRAWINGS

The present invention will be described further in more details, with reference to the attached drawings, in which.

DETAILED DESCRIPTION OF THE FIGURES AND THE INVENTION

Figure 1:
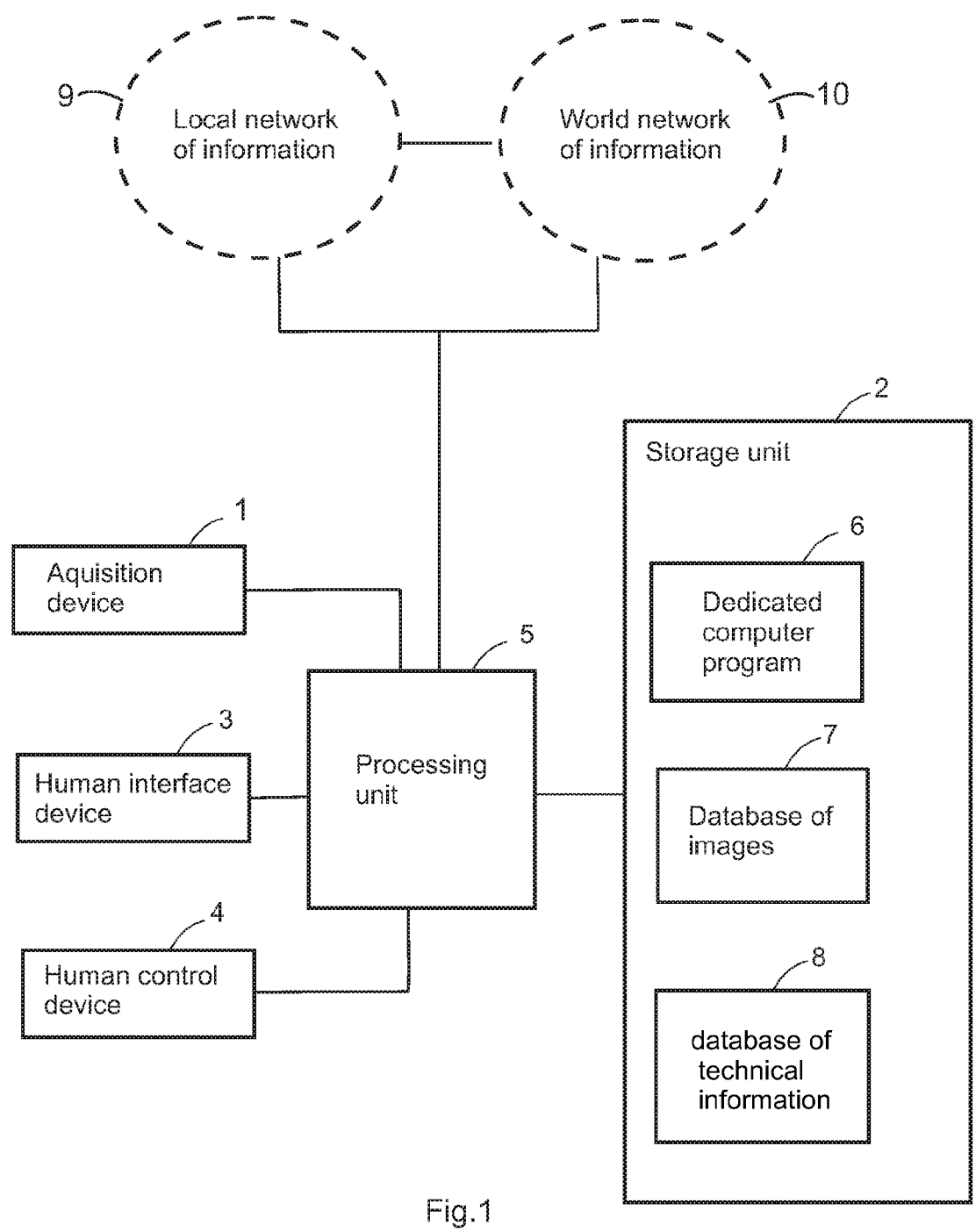
FIG. 1—represents a schematic diagram of the system for the diagnosis of plant anomalies subject matter of the present invention.

FIG. 1 illustrates a diagram of blocks of the system for diagnosing plant anomalies according to a preferred embodiment of the present invention.

The system comprises at least one acquisition device 1 capable of capturing dynamic images in real time of at least one sample of a plant to be diagnosed. Preferably, the image acquisition device 1 consists of a digital microscope (e.g.: electronic microscope DinoLite model AM313T, manufactured by AnMo Eletronics Co.) or a digital video camera. Optionally, devices that capture dynamic images in analog format can be used. In this last case, these analog images must be converted into digital format so that they can be used by the system of the present invention. The use of images in real time ("streaming") is advantageous in comparison with static images (pictures), because users are allowed, due to the use of handheld equipment that can be easily handled in the field, to take pictures directly and to search for an ideal positioning of the plant in a dynamic manner, so as to obtain a better angle for viewing the physiological manifestation of the anomaly, thus making its identification and diagnosis easier. In view of this, filing unnecessary pictures is avoided, so as to spare the acquisition of a memory of higher storage capacity, thereby reducing the costs for implementing the system.

Furthermore, it is worth noting that the acquisition device 1 previously mentioned is preferably locally connected to a trade microcomputer (desktop or notebook), by means of a standard connection USB, Firewire, Wi-fi, Bluetooth, among others, compatible with the application. Preferably, the microcomputer can be a notebook model which can be easily carried to the field due to its portability, not to mention the portability inherent to the camera, which is preferably the aforementioned electronic microscope DinoLite model AM313T. Therefore, the system of the present invention does not require the installation of structured and expensive remote laboratories, which reduces the costs of its implementation and operation.

The system also comprises a storage unit 2 provided with a database of digitalized images 7 of samples of plants affected by anomalies. These images consist of static images (e.g. pictures or drawings in GIF, JPEG, TIFF, BMP format, etc.) and/or dynamic images (e.g. videos or animations in MPEG, MOV, Mp4, Java, Flash format, etc.).

The storage unit 2 also comprises a database of technical information 8 related to such anomalies. Such information consists of data such as causal agent (e.g. plagues), symptomatology, cycle and epidemiology, handling practices, etc. Additionally, the information also consist of products suitable for treating said anomalies, such as suitable compositions, formulae, indications, contraindications, ways and methods of use, biological characteristics of the phytopathogens, among other data which is necessary. Preferably, but not mandatorily, this technical information may be stored in a digital file which can be accessed by a trade program (e.g. Microsoft Word) or a free one (e.g. Acrobat Adobe Reader, Open Office, GSView, Microsoft Internet Explorer, Mozilla Firefox, etc.). In a preferred embodiment of the present invention, the storage unit 2 comprises an integrated circuit ("chip") of non-volatile memory such as EEPROM.

The system also comprises a human interface device 3 capable of displaying digitalized images of the plant samples, so as to allow them to be viewed by, at least, one user. The human interface device 3 preferably consists of a monitor comprising an LCD display or a CRT display.

The system's user actively interacts with the human interface device 3 by means of a human control device 4 of any type, such as a keyboard or a pointing device (e.g. computer mouse).

The acquisition device 1, the storage unit 2, the human interface device 3 and the human control device 4 are operatively associated with a processing unit 5 configured to run a dedicated computer program 6 which is preferably stored at the storage unit 2.

These associations among the pieces and components of the system can be performed by any known electric/electronic communication means (transmitting/receiving), such as fibers, cables, integrated circuits, tracks of PCB boards, wireless, etc.

The processing unit 5 consists of a microprocessor or a microcontroller, such as a microprocessor for use on a personal computer such as: Intel (Celeron, Dual Core, Core 2 Duo, Core 2 Quad, etc.), AMD, Via, etc.

In a preferred embodiment of the present invention, the dedicated computer program 6 consists of an independent application which can be run at an operating system such as Microsoft Windows and/or a Linux distribution.

Optionally, the dedicated computer program 6 consists of a dependent application which can be run on a free Internet browser, such as Microsoft Internet Explorer or Mozilla Firefox, so as to reduce the costs for implementing the system, once it is not necessary to purchase expensive trade programs.

Thus, unlike the system disclosed by document U.S. Pat. No. 6,014,451 (or the corresponding Brazilian patent application PI 9813086-2), the main functions of the system of the present invention are controlled by a single dedicated computer program 6, which, apart from not requiring a high processing capacity of hardware, optimizes the data flow among its pieces (acquisition device 1, storage unit 2, human interface device 3 and human control device 4).

Figure 2:
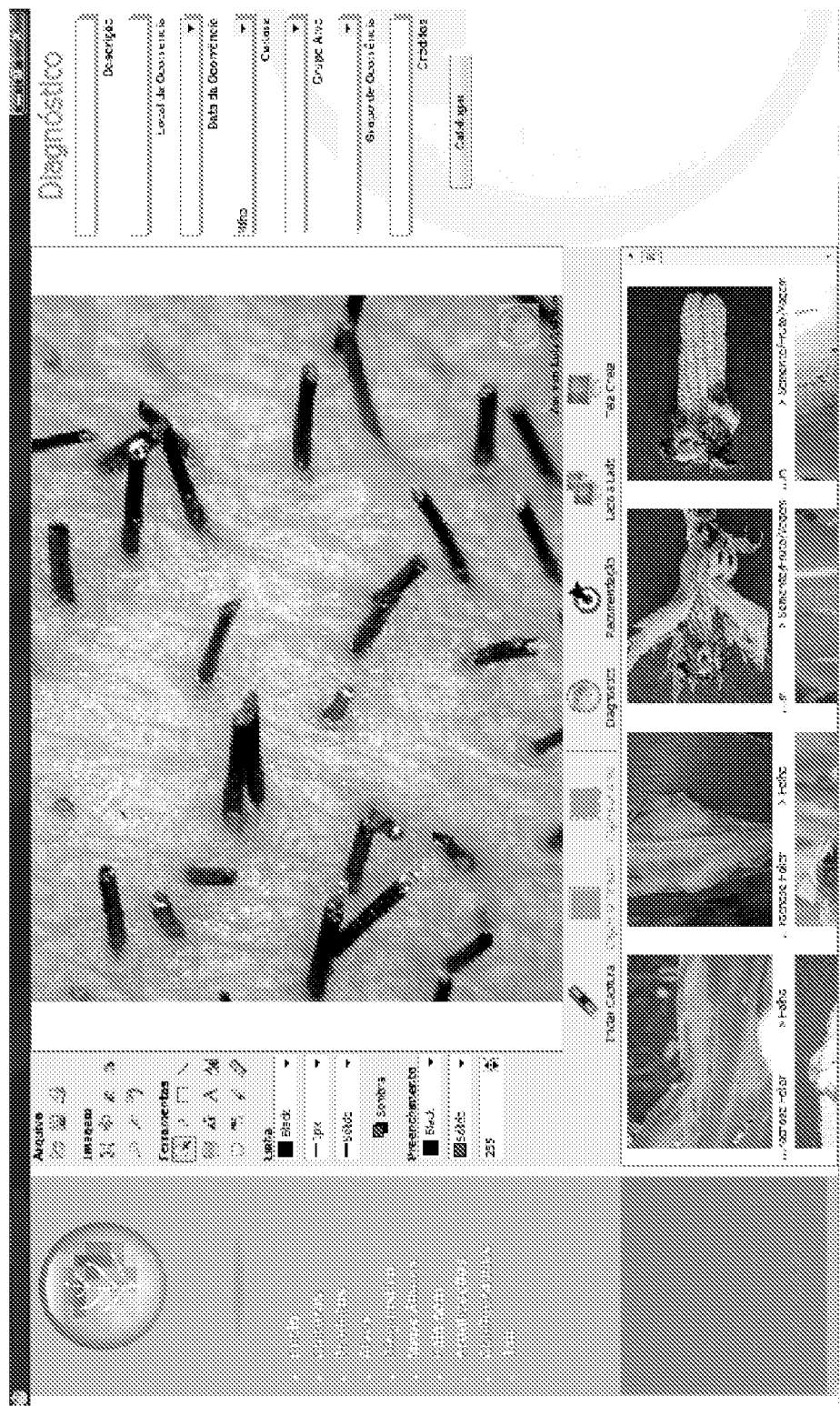
FIG. 2—represents an image of a first screen displayed in the human interface device of the system illustrated in FIG. 1, highlighting a captured image of the plant to be diagnosed.
Figure 3:
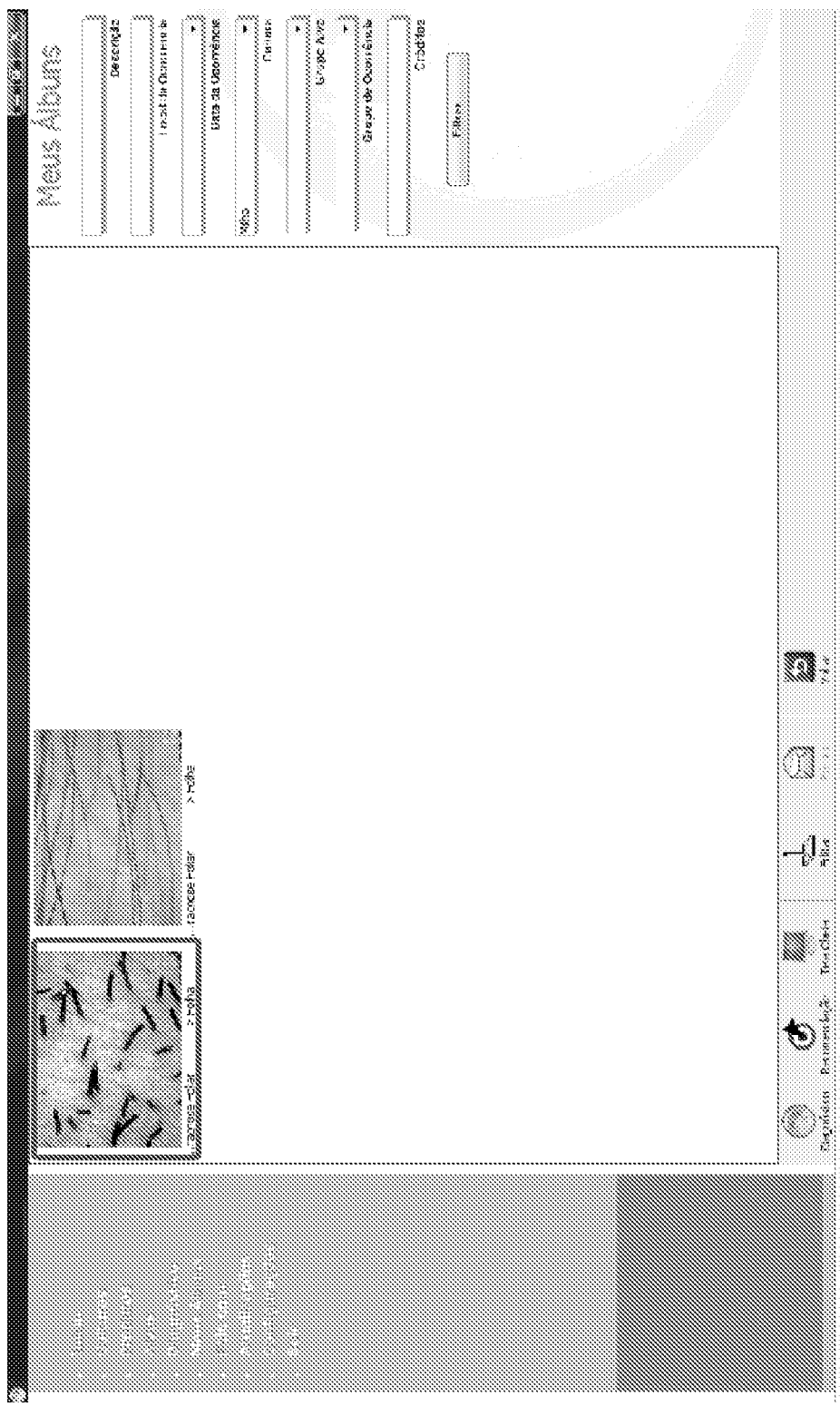
FIG. 3—represents an image of a second screen displayed in the human interface device of the system illustrated in FIG. 1, highlighting the display side by side of the captured image of the plant to be diagnosed and an image selected from the database of images.

The dedicated computer program 6 is able to allow the display of the image of the plant sample to be diagnosed and the digitalized image of the plant sample filed in the database of images from the storage unit 2 simultaneously on the human interface device 3, as shown in FIGS. 2 and 3. Thus, the images are arranged "side by side", allowing users to visually compare them in a simple, fast and easy manner. FIG. 2 illustrates a screen which represents a situation in which the user is still selecting the most appropriate image from the database of images 7. FIG. 3 illustrates a screen which represents a situation in which the user already selected the most appropriate image from the database of images 7.

Besides, the dedicated computer program 6 allows for the graphic manipulation of the plant images shown in the human interface device 3 by means of the human control device 4. Such graphic manipulation of images is allowed by means of edition tools displayed on the human interface device 3 and accessible by the human control device 4. As it can be observed in FIG. 2, these edition tools allow for selecting, cutting, enlarging, shortening, highlighting, enhancing, resampling, changing properties (brightness, color, contrast), creating lines, angles, dimensional rays, text boxes, freehand drawing, etc., providing functionalities which promote a more accurate identification of the plant anomaly, in a simple and intuitive manner.

Such situation emphasizes the concept of portability and simplicity of the present invention, where a plant with a disease can be photographed in the field, in the middle of a plantation, by a microscope linked to a notebook, and a comparative picture, located in the database of images 7, at the storage unit 2, may be received in field by a wireless communication network, such as any mobile telephony network.

Figure 4:
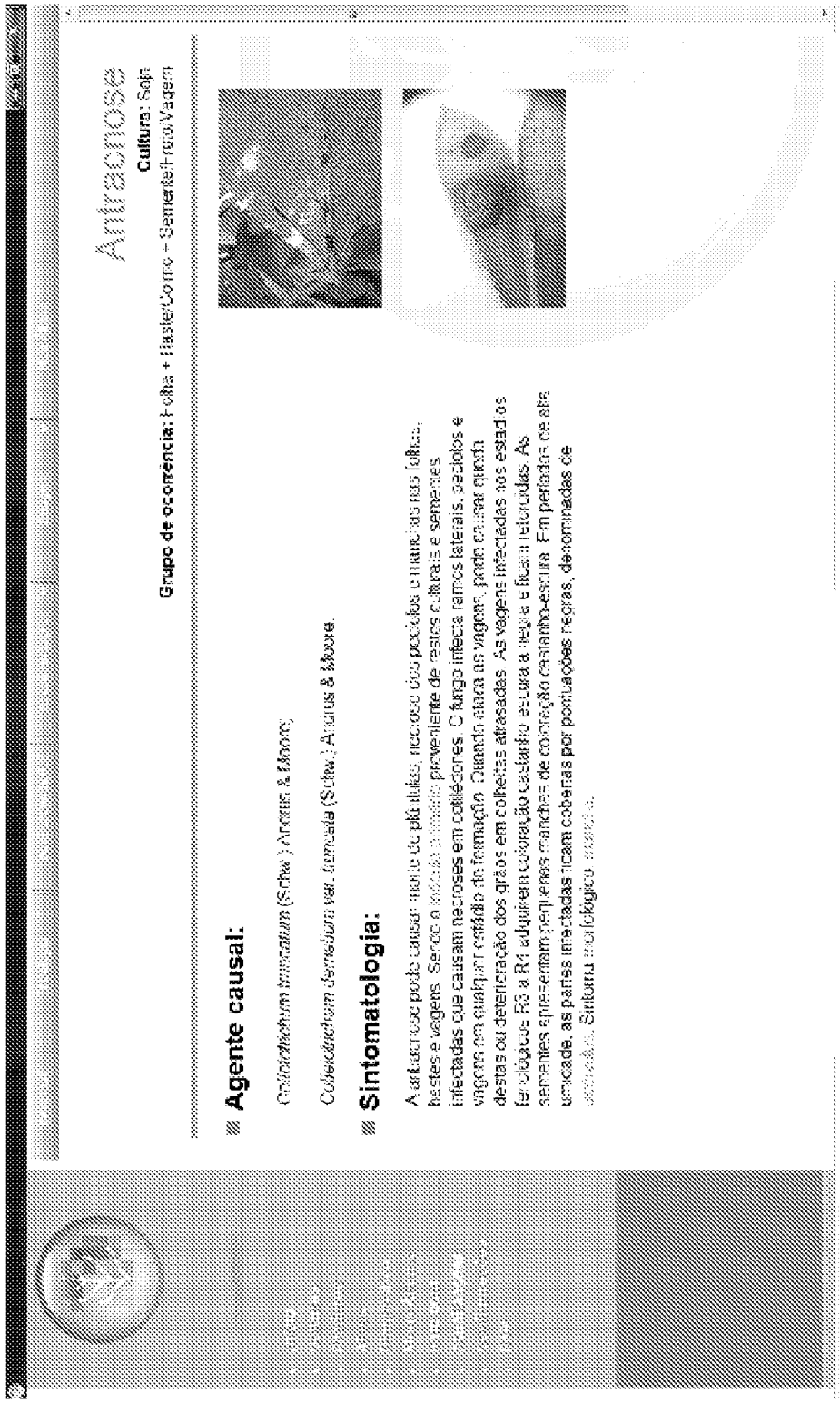
FIG. 4—represents an image of a third screen displayed in the human interface device of the system illustrated in FIG. 1, highlighting information related to the diagnosed anomaly.
Figure 5:
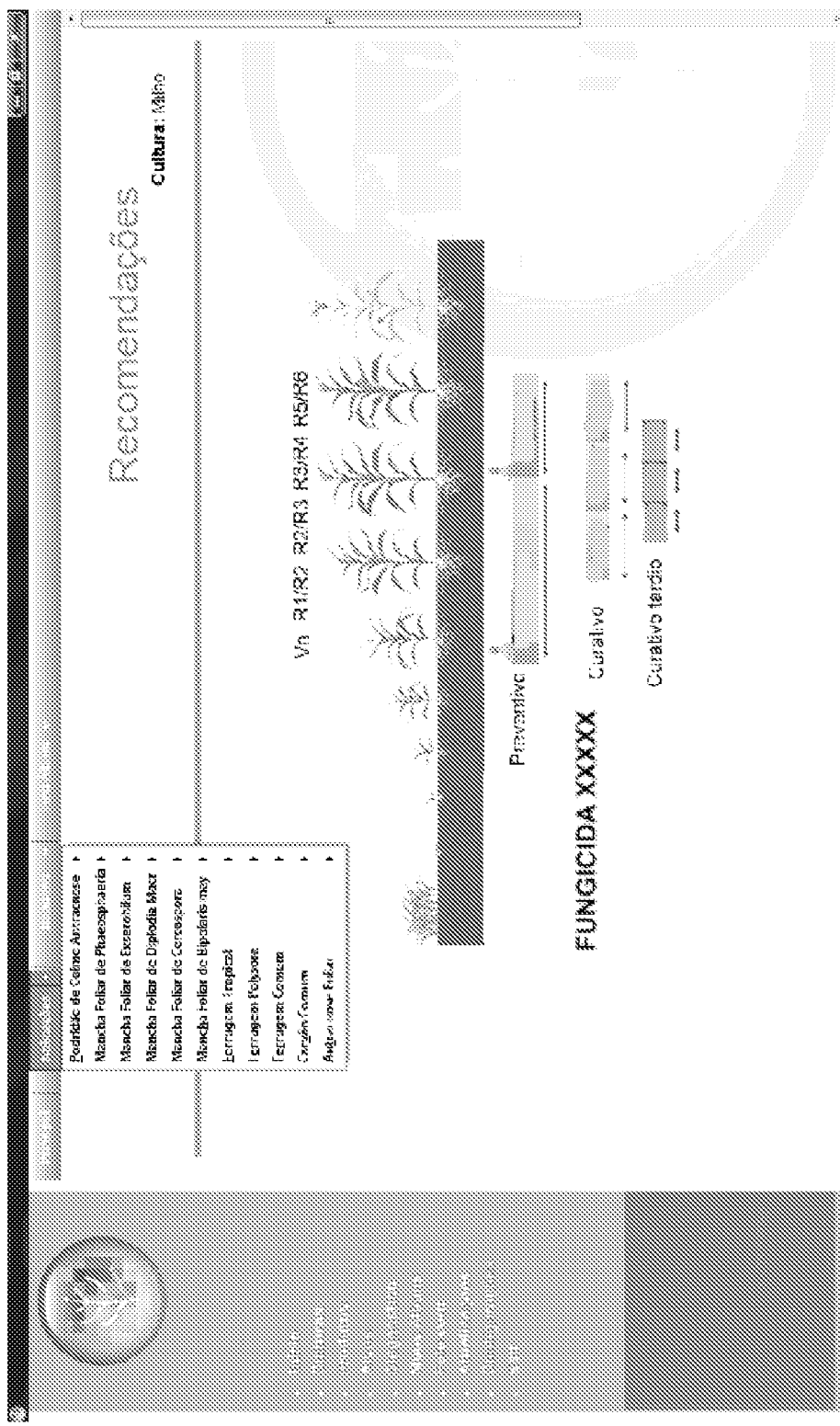
FIG. 5—represents an image of a fourth screen displayed in the human interface device of the system illustrated in FIG. 1, highlighting information related to the treatment of the diagnosed anomaly.

After the identification and diagnosis of the anomaly, the dedicated computer program 6 provides information related to the causal agent (e.g. plagues), symptomatology, cycle and epidemiology, handling practices, etc, as it can be seen in FIG. 4.

Moreover, the dedicated computer program 6 is capable of automatically providing information on, at least, one product and/method suitable for treating the anomaly diagnosed by means of the human interface device 3, as shown by picture 5. These pieces of information are stored in the database of information 8 from the storage device 2. Therefore, it is possible to start the treatment and control of the plant anomalies immediately after the diagnosis thereof, once it is not necessary the presence of a human specialist to contact the user by telephone, e-mail or letter, unlike the system disclosed by document U.S. Pat. No. 6,014,451 (PI 9813086-2), which could delay the beginning of the anomaly treatment, resulting in significant losses, not to mention the higher costs arising from the need of this professional and from the existence of such remote laboratories, imperative in the prior art in question and whose disadvantages have been previously commented.

Additionally, the processing unit 5 is configured to allow for searching in the database of images 7 and in the database of technical information 8 by means of searching filters by running the dedicated computer program 6. Such filters comprise, for instance, the plant species, the crop cultivation, the origin of the plant, the climate and/or the parts of the plant (leaf, stem, root, etc.).

Figure 6:
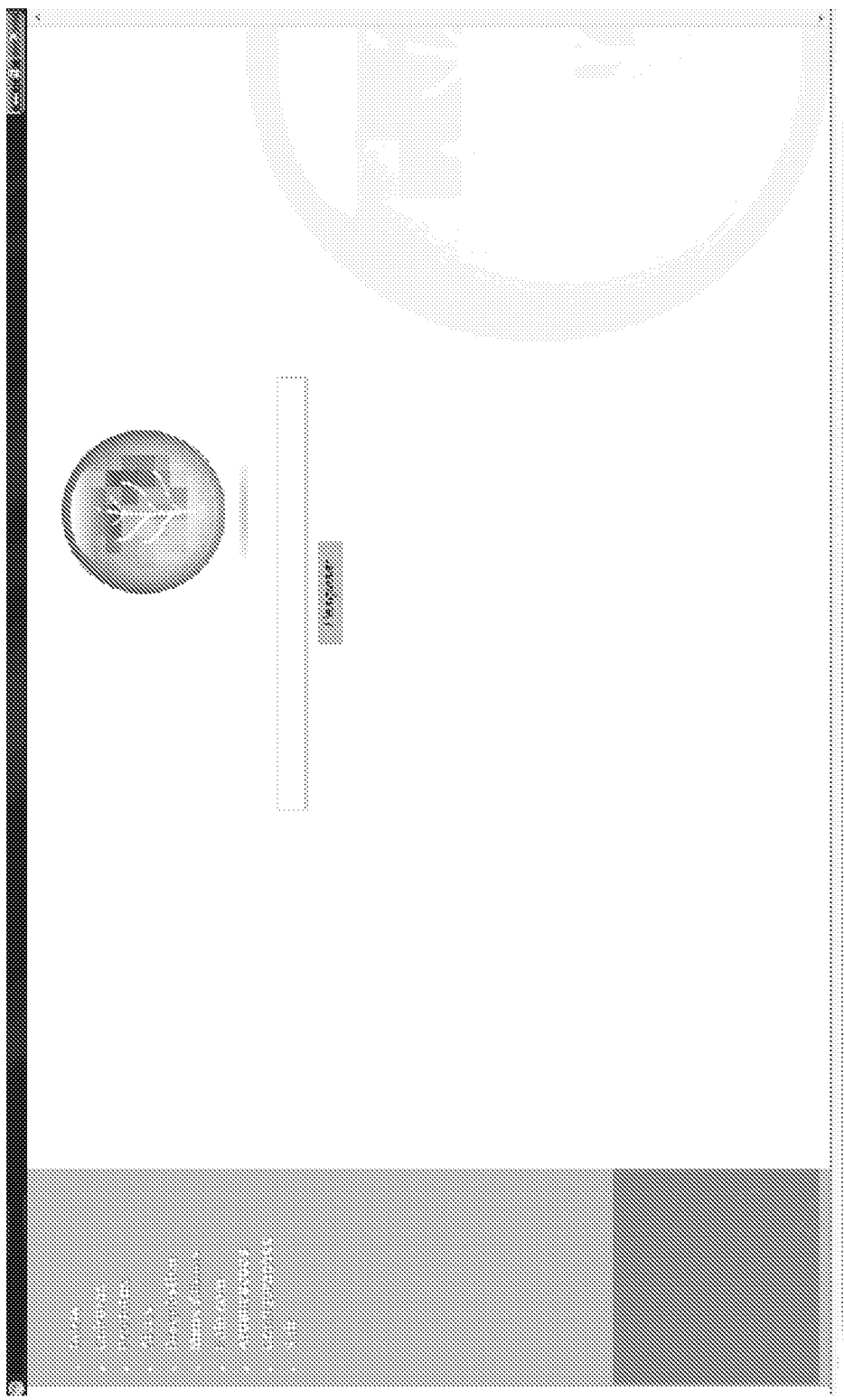
FIG. 6—represents an image of a fifth screen displayed in the human interface device of the system illustrated in FIG. 1, highlighting a field of research by keyword.
Figure 7:
FIG. 7—represents an image of a sixth screen displayed in the human interface device of the system illustrated in FIG. 1, highlighting results filtered from the research by keyword.

As it can be seen in FIGS. 6 and 7, the system also allows for performing a search in the database of images 7 and in the database of technical information 8 by means of, at least, a keyword added by the user to the dedicated computer program 6 run by the processing unit 5.

In a preferred embodiment of the present invention, the system is associated to a world network of information 10, such as the Internet, so as to share images and information contained in the storage unit 2.

Optionally, the system is associated to a local network of information 9, such as private Intranet (internal network of a university or company).

In both situations, the processing unit 5 is configured to allow for publishing the image captured by the acquisition device 1 in the world and or local network of information by running the dedicated computer program 6. Evidently, the local network of information 9 may be associated to the world network of information 10.

Figure 9:
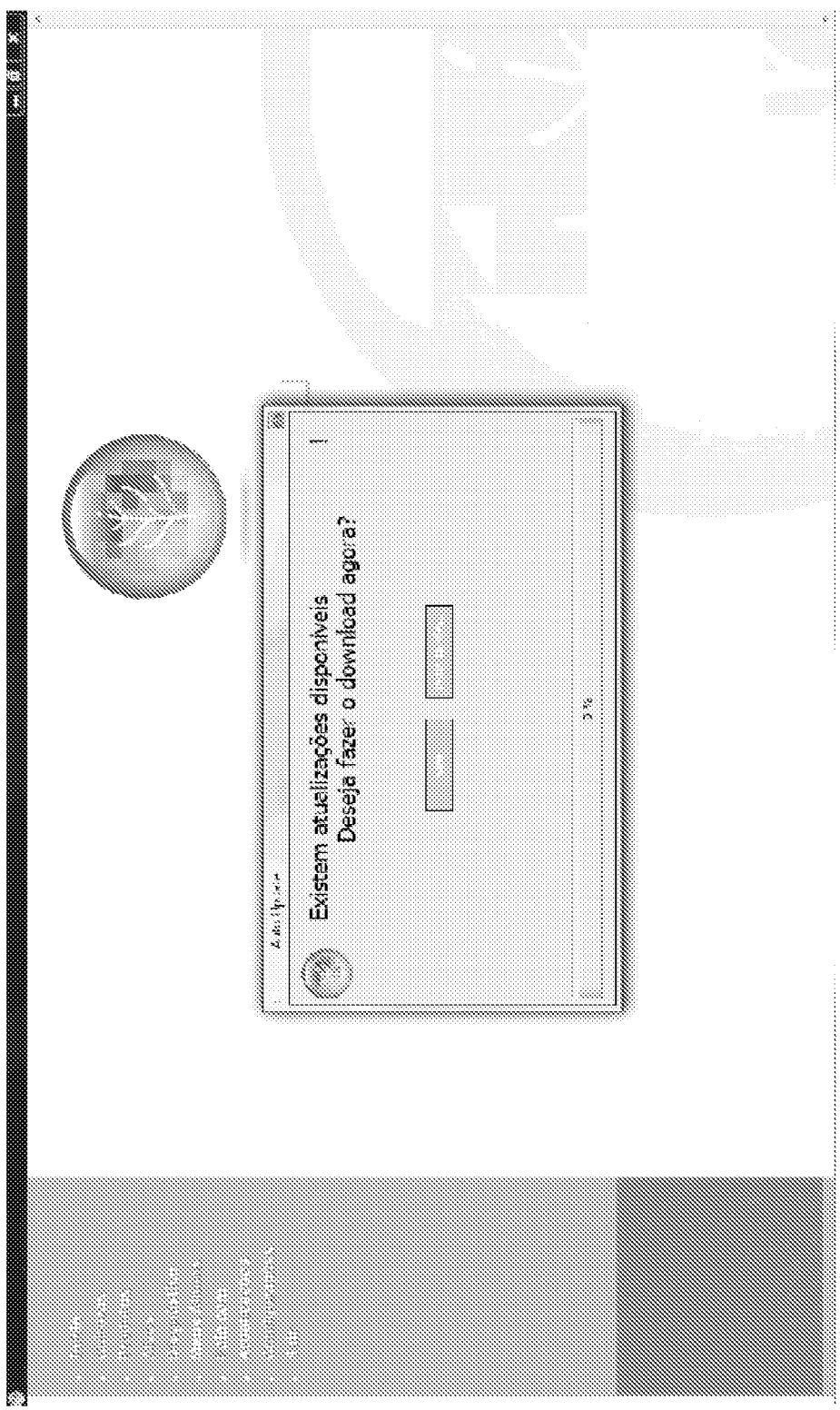
FIG. 9—represents an image of an eighth screen displayed in the human interface device of the system illustrated in FIG. 1, highlighting the automatic update of the dedicated computer program.

Still, the processing unit 5 is also configured to update the database of images 7 and the database of technical information 8 from the storage unit 2 automatically and periodically through the Internet and/or Intranet by running the dedicated computer program 6, as shown by FIG. 9. Alternatively, updating can be manually performed by the users themselves. Evidently, the other functions of the dedicated computer program 6 can also be automatically updated through the Internet and/or Intranet.

Figure 8:
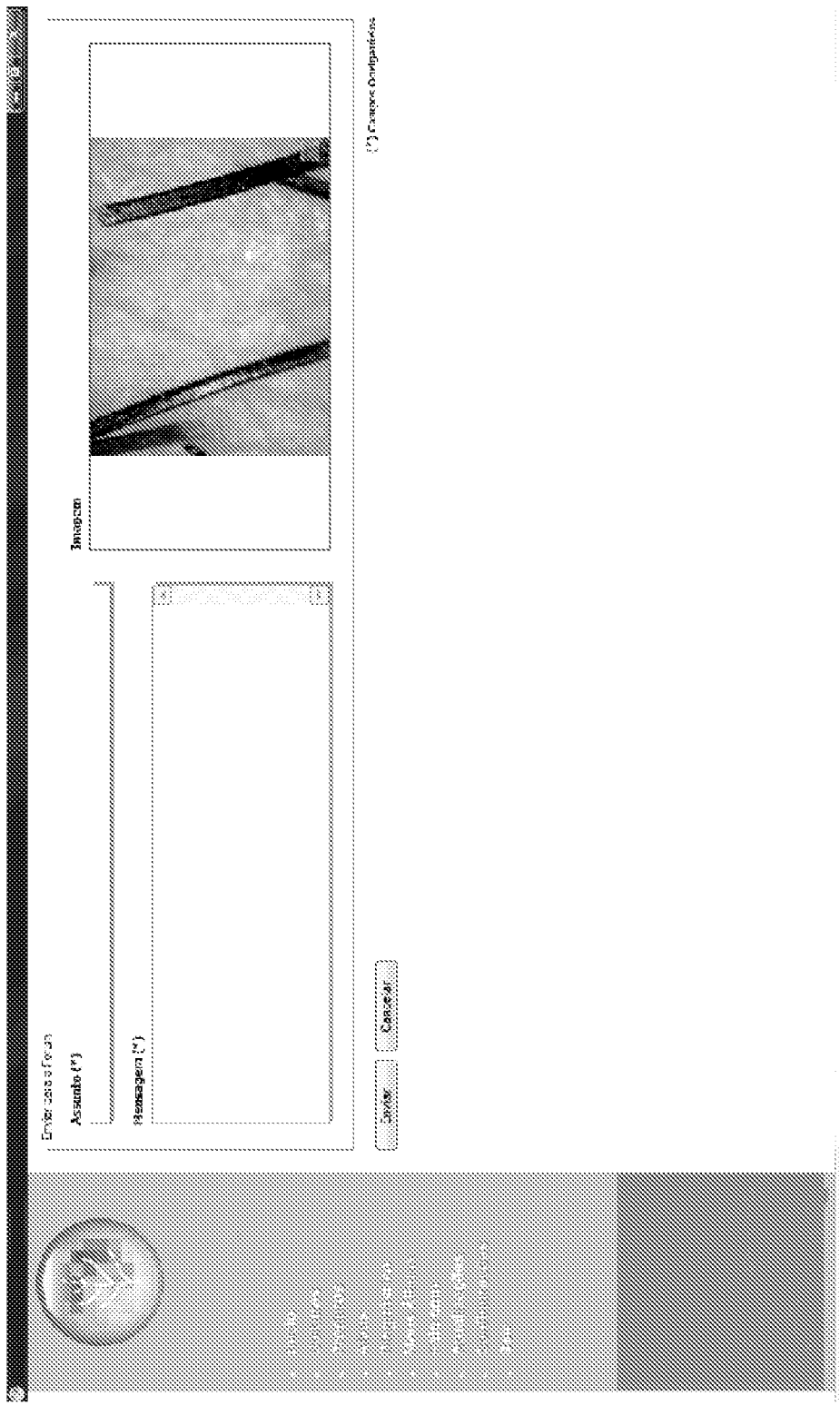
FIG. 8—represents an image of a seventh screen displayed in the human interface device of the system illustrated in FIG. 1, highlighting the interaction of the user with a forum (discussion group)

The dedicated computer program 6 provides communication links which allow users to interact by means of forums, instant messengers, chat rooms, audio/video conferences, in order to share experiences and information, as shown by FIG. 8. The dedicated computer program 6 can also provide links which lead to Internet or Intranet pages that contain additional information on plants, anomalies, diseases, plagues, treatment methods, recommended products, etc.

It is worth noting that the system of the present invention can be also used as research literature by scientists, farmers, students, phytopathologists, agronomists and other interested people, once the storage unit 2 contains a wide range of data, periodically updated, concerning the technical information and images of the plants affected by anomalies. Evidently, in this specific application, it is not necessary to use an acquisition device 1 once the system will only be used for consultation purposes and not for comparison.

From the viewpoint of the system's user, the dedicated computer program 6 comprises four major modules:

1—Research module: module used for purposes of research, study, consultation and analysis of images and technical information concerning known plant anomalies. Thus, in this module, the user of the system has direct access to the database of images 7 and to the database of technical information 8 from the storage device 2.

2—Diagnosis module: module used for purposes of identification/analysis of plant anomalies by visually comparing images of a plant to be diagnosed with images of plants affected by anomalies stored in the database of images 7. This module also offers information and recommended methods for treating the diagnosed anomalies.

3—Module of researchers interchange: module used for purposes of communication/interaction among scientists, students, phytopathologists, farmers, for the exchange of information and experiences through a local/world network of information.

4—Update module: module used to update the dedicated computer program 6 through the Internet and/or Intranet.

Therefore, the present invention discloses an unprecedented solution which allows for diagnosing and treating plant anomalies, apart from providing a source of studies/research and, also, enabling interaction with other researchers, scientists, scholars, farmers, agronomists and phytopathologists by means of a low cost system, which can be run quickly and used in a simple and easy manner.

In one embodiment, the system according to the invention is characterized in that it is associated to a local network of information (9), the processing unit (5) being configured to allow for sharing data contained in the storage device (2) at the local network of information (9) by running the dedicated computer program (6).

In another embodiment, the system according to the invention is characterized in that it is associated to a world network of information (10), the processing unit (5) being configured to allow for sharing data contained in the storage device (2) at the world network of information (10) by running the dedicated computer program (6).

In another embodiment, the system according to the invention is characterized in that the processing unit (5) is configured to update the database of images (7) and the database of information (8) from the storage unit (2) automatically and periodically through the local network of information (9) and/or through the world network of information (10) by running the dedicated computer program (6).

In another embodiment, the system according to the invention is characterized in that the graphic manipulation of images is allowed by means of edition tools displayed on the human interface device (3) and accessible by the human control device (4).

In another embodiment, the system according to the invention is characterized in that the processing unit (5) is configured to allow for a search in the database of images (7) and in the database of information (8) by means of searching filters by running the dedicated computer program (6).

In another embodiment, the system according to the invention is characterized in that the processing unit (5) is configured to allow for a search in the database of images (7) and in the database of information (8) by means of at least a keyword by running the dedicated computer program (6).

In another embodiment, the system according to the invention is characterized in that the dedicated computer program (6) is stored in the storage unit (2).

Below, there are two examples of the utilization of the present invention.

EXAMPLE 1

Identification of Asian Soybean Rust

The Asian Soybean Rust consists of an important anomaly or disease that occurs in the soy culture, and, due to its extreme aggressiveness, it is capable of decimating whole plantations in a few days if the diagnosis is not made, or if it is performed too late.

It is known that the most effective method to control this anomaly is by applying specific fungicides preventively, that is, when there are no symptoms or, at the worst case, when they begin to manifest themselves. These symptoms, at their early stage, can not be viewed at with the naked eye, and it is necessary to use high proximity (zoom) microscopes so that they can be correctly identified. The most propitious phase for the surge of this anomaly is during the plants reproductive stage, that is, after the crop blossoms.

The system disclosed by the present invention allows for detecting the presence of spores of Asian soybean rust on a commercial plantation which is still under vegetative stage. At this stage, it is less likely that disease will manifest itself, once the higher rates of manifestation are observed after the vegetative stage, that is, during the crop reproductive stage.

Such spores can be registered by the acquisition device 1 as images which, in turn, can be registered in the storage device 2 to be later handled by the human control device 4 and, finally, be broadcast to a world network of information 10.

Thus, as the focuses of this disease can not be detected in the vegetative stage with the naked eye, the system's interchange module allows for sending warning messages by e-mail to cooperatives and resellers, in order to warn producers on the surge of the disease, so that they can then start efficient control applications in a preventive manner.

Accordingly, the diagnosis system allows quick prophylactic preventive measures of control to be taken as soon as the disease is identified.

EXAMPLE 2

Identification of Asian Rust Focus

The resources provided by the diagnosis system of the present invention allow for identifying the presence of spores in a guaxa plant (which emerges due to grains fallen in the land) under stage of grain filling (R 5.4).

In this case, it is possible to capture an image of the plant by means of the acquisition device 1 and to register it on the storage unit 2, so that it can be handled and enlarged by using the human interface device 3, the human control device 4 and the processing unit 5, in order to detect the presence of the spores.

From the interchange module, it is possible to send instant warning messages to producers, distribution channels and consultants by e-mail through the world network of information 10 (Internet), informing the need of preventively applying fungicides in the region, since the crop can start experiencing a critical stage (spores present in the air).

This way, by using the system, it is possible to prevent the incidence of rust in a certain region and its neighboring areas.

After describing an example of preferred embodiment, it shall be understood that the scope of the present invention encompasses other possible variations, being limited only by the contents of the attached claims, where the possible equivalents are included.

The invention claimed is:

1. A system for the diagnosis of plant anomalies comprising:

at least one acquisition device configured for capturing images in real time of at least one sample of a plant to be diagnosed;

at least one storage unit comprising a database of digitalized images of samples of plants affected by anomalies and a database of technical information related to said anomalies;

at least one human interface device configured for displaying digitalized images of plant samples from the acquisition device and the storage unit;

at least one human control device configured for allowing for an active interaction between a user and the human interface device; and at least one processing unit operatively associated to the acquisition device, to the storage unit, to the human interface device and to the human control device, wherein the processing unit is configured to run a dedicated computer program such program configured for:

allowing access to the database of digitalized images and allowing searching in the database of digitalized images thereby allowing the display of the image of the sample of the plant to be diagnosed and an image of the digitalized images of the samples of the plant filed in the database of images from the storage unit simultaneously in the human interface device;

automatically providing information on at least one product and/or method suitable for treating an anomaly diagnosed by means of the human interface device by means of information that is stored in the database of technical information of the storage device; and allowing for a graphic manipulation of the plant images shown on the human interface device by means of the human control device;

wherein the at least one acquisition device, the at least one human interface device, the at least one human control device, and the at least one processing unit are portable and are configured to allow a user to diagnose a plant anomaly with the system in the field.

2. The system of claim 1, wherein the system is associated with a local network of information, and wherein the processing unit is configured to allow for sharing data contained in the storage device at the local network of information by running the dedicated computer program.

3. The system of claim 2, wherein the processing unit is configured to update the database of images and the database of information from the storage unit automatically and periodically through the local network of information by running the dedicated computer program.

4. The system of claim 1, wherein the system is associated to a world network of information, the processing unit being configured to allow for sharing data contained in the storage device at the world network of information by running the dedicated computer program.

5. The system of claim 4, wherein the processing unit is configured to update the database of images and the database of information from the storage unit automatically and periodically through the world network of information by running the dedicated computer program.

6. The system of claim 1, wherein the graphic manipulation of images is allowed by means of edition tools displayed on the human interface device and accessible by the human control device.

7. The system of claim 1, wherein the processing unit is configured to allow for a search in the database of images and in the database of information by means of searching filters by running the dedicated computer program.

8. The system of claim 1, wherein the processing unit is configured to allow for a search in the database of images and in the database of information by means of at least a keyword by running the dedicated computer program.

9. The system of claim 1, wherein the dedicated computer program is stored in the storage unit.

10. The system of claim 1, wherein the plant anomalies are caused by bacteria, virus, fungi, nematodes or insects.

11. The system of claim 1, wherein the acquisition device is locally associated with a microcomputer.

12. The system of claim 11, wherein the processing unit is used on the microcomputer.

13. The system of claim 11, wherein the human interface device and the human control device is locally associated with the microcomputer.

\* \* \* \* \*